US008915952B2

(12) United States Patent
Rudakov

(10) Patent No.: US 8,915,952 B2
(45) Date of Patent: Dec. 23, 2014

(54) METHOD FOR TREATING ANEURYSMS

(75) Inventor: Leon Rudakov, Belmont, CA (US)

(73) Assignee: Merlin MD Pte Ltd., Northtech (SG)

(*) Notice: Subject to any disclaimer, the term of this patent is extended or adjusted under 35 U.S.C. 154(b) by 1514 days.

(21) Appl. No.: 11/547,100

(22) PCT Filed: Oct. 15, 2004

(86) PCT No.: PCT/SG2004/000338
§ 371 (c)(1),
(2), (4) Date: Sep. 29, 2006

(87) PCT Pub. No.: WO2005/094725
PCT Pub. Date: Oct. 13, 2005

(65) Prior Publication Data
US 2007/0191924 A1    Aug. 16, 2007

(30) Foreign Application Priority Data
Mar. 31, 2004   (SG) .............................. 200401735-6

(51) Int. Cl.
A61F 2/06     (2013.01)
A61B 17/12    (2006.01)
A61F 2/07     (2013.01)
A61F 2/915    (2013.01)
A61F 2/82     (2013.01)
A61F 2/89     (2013.01)
A61F 2/30     (2006.01)
A61F 2/958    (2013.01)

(52) U.S. Cl.
CPC ..... *A61B 17/12022* (2013.01); *A61F 2002/075* (2013.01); *A61F 2002/91525* (2013.01); *A61F 2002/91541* (2013.01); *A61F 2/07* (2013.01); *A61B 17/12118* (2013.01); *A61F 2/915* (2013.01); *A61F 2002/823* (2013.01); *A61F 2/89* (2013.01); *A61F 2250/0037* (2013.01); *A61B 17/1214* (2013.01); *A61F 2250/0098* (2013.01); *A61F 2002/3008* (2013.01); *A61B 17/12186* (2013.01); *A61F 2002/91558* (2013.01); *A61F 2002/91566* (2013.01); *A61F 2/958* (2012.01)
USPC ...................................... 623/1.15

(58) Field of Classification Search
CPC ............ A61F 2002/91575; A61F 2/89; A61F 2002/91541; A61F 2002/91533
USPC ............. 623/1.31, 1.35, 1.15, 1.3, 1.37, 1.16; 606/200
See application file for complete search history.

(56) References Cited

U.S. PATENT DOCUMENTS 4,416,028 A   11/1983 Eriksson et al.
4,503,569 A    3/1985 Dotter
(Continued)

FOREIGN PATENT DOCUMENTS

EP    0754435      1/1997
EP    0 864 301    9/1998
(Continued)

OTHER PUBLICATIONS

Chatterjee, S., Lactosylceramide stimulates aortic smooth muscle cell proliferation, Biochemical and Biophysical Research Communications, Dec. 16, 1991, 554-561, vol. 181, No. 2, Academic Press, Orlando, FL.

(Continued)

Primary Examiner — Thomas McEvoy
Assistant Examiner — Julie A Szpira
(74) Attorney, Agent, or Firm — James W. Hill; Nathan Smith; McDermott Will & Emery LLP

(57) ABSTRACT

A method for treating a bifurcation aneurysm, the aneurysm having an aneurysm neck, by positioning a first mechanically expandable device in a first bifurcation branch proximate to the aneurysm neck; positioning a second mechanically expandable device in a second bifurcation branch proximate to the aneurysm neck; and expanding the mechanically expandable devices to constrict the aneurysm neck such that blood circulation to the bifurcation aneurysm is reduced.

20 Claims, 15 Drawing Sheets

(56) References Cited

U.S. PATENT DOCUMENTS

| | | | |
|---|---|---|---|
| 5,041,441 A | 8/1991 | Radin et al. | |
| 5,234,457 A | 8/1993 | Anderson | |
| 5,356,423 A | 10/1994 | Tihon et al. | |
| 5,405,377 A | 4/1995 | Cragg | |
| D359,802 S | 6/1995 | Fontaine | |
| 5,421,955 A | 6/1995 | Lau et al. | |
| 5,443,458 A | 8/1995 | Eury | |
| 5,514,154 A | 5/1996 | Lau et al. | |
| 5,562,725 A | 10/1996 | Schmitt et al. | |
| 5,589,563 A | 12/1996 | Ward et al. | |
| 5,601,593 A | 2/1997 | Freitag | |
| 5,620,763 A | 4/1997 | House et al. | |
| 5,630,840 A | 5/1997 | Mayer | |
| 5,632,840 A | 5/1997 | Campbell | |
| 5,639,278 A | 6/1997 | Dereume et al. | |
| 5,700,285 A | 12/1997 | Myers et al. | |
| D390,957 S | 2/1998 | Fontaine | |
| 5,716,393 A * | 2/1998 | Lindenberg et al. | 623/1.2 |
| 5,718,973 A | 2/1998 | Lewis et al. | |
| 5,735,893 A | 4/1998 | Lau et al. | |
| 5,744,515 A | 4/1998 | Clapper | |
| 5,766,238 A | 6/1998 | Lau et al. | |
| 5,769,884 A | 6/1998 | Solovay | |
| 5,810,870 A | 9/1998 | Myers et al. | |
| 5,843,027 A * | 12/1998 | Stone et al. | 604/509 |
| 5,843,172 A | 12/1998 | Yan | |
| 5,858,556 A | 1/1999 | Eckert et al. | |
| 5,866,217 A | 2/1999 | Stenoien et al. | |
| 5,902,475 A | 5/1999 | Trozera et al. | |
| 5,925,075 A | 7/1999 | Myers et al. | |
| 5,948,018 A | 9/1999 | Dereume et al. | |
| 5,951,599 A | 9/1999 | McCrory | |
| 5,993,489 A | 11/1999 | Lewis et al. | |
| 6,001,123 A | 12/1999 | Lau | |
| 6,010,530 A | 1/2000 | Goicoechea | |
| 6,024,765 A | 2/2000 | Wallace et al. | |
| 6,027,811 A | 2/2000 | Campbell et al. | |
| 6,033,435 A | 3/2000 | Penn et al. | |
| 6,036,720 A | 3/2000 | Abrams et al. | |
| 6,056,775 A * | 5/2000 | Borghi et al. | 623/1.16 |
| 6,056,776 A | 5/2000 | Lau et al. | |
| 6,066,167 A | 5/2000 | Lau et al. | |
| 6,139,564 A | 10/2000 | Teoh | |
| 6,140,127 A | 10/2000 | Sprague | |
| 6,168,610 B1 | 1/2001 | Marin et al. | |
| 6,174,328 B1 | 1/2001 | Cragg | |
| 6,217,607 B1 | 4/2001 | Alt | |
| 6,240,616 B1 | 6/2001 | Yan | |
| 6,240,948 B1 | 6/2001 | Hansen, III et al. | |
| 6,248,190 B1 | 6/2001 | Stinson | |
| 6,258,120 B1 * | 7/2001 | McKenzie et al. | 623/1.36 |
| 6,270,523 B1 | 8/2001 | Herweck et al. | |
| 6,309,367 B1 | 10/2001 | Boock | |
| 6,312,463 B1 | 11/2001 | Rourke et al. | |
| 6,315,791 B1 | 11/2001 | Gingras et al. | |
| 6,371,980 B1 * | 4/2002 | Rudakov et al. | 623/1.12 |
| 6,409,754 B1 | 6/2002 | Smith et al. | |
| 6,416,474 B1 | 7/2002 | Penner et al. | |
| 6,436,132 B1 | 8/2002 | Patel et al. | |
| 6,451,050 B1 | 9/2002 | Rudakov et al. | |
| 6,451,052 B1 | 9/2002 | Burmeister et al. | |
| 6,454,780 B1 | 9/2002 | Wallace | |
| 6,485,507 B1 | 11/2002 | Walak et al. | |
| 6,488,701 B1 | 12/2002 | Nolting et al. | |
| 6,508,832 B1 | 1/2003 | Jalisi et al. | |
| 6,517,571 B1 | 2/2003 | Brauker et al. | |
| 6,524,336 B1 * | 2/2003 | Papazolgou et al. | 623/1.35 |
| 6,527,802 B1 | 3/2003 | Mayer | |
| 6,533,905 B2 | 3/2003 | Johnson et al. | |
| 6,547,815 B2 | 4/2003 | Myers | |
| 6,582,461 B1 | 6/2003 | Burmeister et al. | |
| 6,582,652 B2 | 6/2003 | Craig | |
| 6,602,281 B1 * | 8/2003 | Klein | 623/1.15 |
| 6,613,072 B2 | 9/2003 | Lau et al. | |
| 6,613,074 B1 | 9/2003 | Mitelberg et al. | |
| 6,623,520 B2 | 9/2003 | Jalisi | |
| 6,652,574 B1 | 11/2003 | Jayaraman | |
| D484,979 S | 1/2004 | Fontaine | |
| 6,673,108 B2 | 1/2004 | Zilla et al. | |
| 6,676,701 B2 | 1/2004 | Rourke et al. | |
| 6,679,910 B1 | 1/2004 | Granada | |
| 6,695,833 B1 | 2/2004 | Frantzen | |
| 6,695,876 B1 | 2/2004 | Marotta et al. | |
| 6,699,276 B2 | 3/2004 | Sogard et al. | |
| 6,706,061 B1 | 3/2004 | Fischell et al. | |
| 6,719,782 B1 | 4/2004 | Chuter | |
| 6,736,844 B1 | 5/2004 | Glatt et al. | |
| 6,796,997 B1 | 9/2004 | Penn et al. | |
| 6,802,851 B2 | 10/2004 | Jones et al. | |
| 6,805,706 B2 | 10/2004 | Solovay et al. | |
| 6,818,013 B2 | 11/2004 | Mitelberg et al. | |
| 6,821,293 B2 | 11/2004 | Pinchasik | |
| 6,855,154 B2 | 2/2005 | Abdel-Gawwad | |
| 6,899,727 B2 | 5/2005 | Armstrong et al. | |
| 6,936,055 B1 | 8/2005 | Ken et al. | |
| 6,949,116 B2 | 9/2005 | Solymar et al. | |
| 6,979,349 B1 | 12/2005 | Dang et al. | |
| 7,029,493 B2 | 4/2006 | Majercak et al. | |
| 7,041,127 B2 * | 5/2006 | Ledergerber | 623/1.31 |
| 7,041,129 B2 | 5/2006 | Rourke et al. | |
| 7,060,091 B2 | 6/2006 | Killion et al. | |
| 7,105,019 B2 | 9/2006 | Hojeibane | |
| 7,125,419 B2 * | 10/2006 | Sequin et al. | 623/1.35 |
| 7,153,322 B2 | 12/2006 | Alt | |
| 7,169,174 B2 | 1/2007 | Fischell et al. | |
| 7,258,697 B1 | 8/2007 | Cox et al. | |
| D553,746 S | 10/2007 | Fliedner | |
| D553,747 S | 10/2007 | Fliedner | |
| 7,306,622 B2 | 12/2007 | Jones et al. | |
| 7,311,726 B2 | 12/2007 | Mitelberg et al. | |
| 7,686,846 B2 * | 3/2010 | Laborde et al. | 623/1.35 |
| 8,075,609 B2 | 12/2011 | Penn et al. | |
| 2002/0035394 A1 | 3/2002 | Fierens et al. | |
| 2002/0042646 A1 | 4/2002 | Wall | |
| 2002/0045931 A1 | 4/2002 | Sogard et al. | |
| 2002/0049495 A1 | 4/2002 | Kutryk et al. | |
| 2002/0065546 A1 | 5/2002 | Machan et al. | |
| 2002/0111543 A1 | 8/2002 | Penner et al. | |
| 2002/0133224 A1 | 9/2002 | Bajgar et al. | |
| 2002/0151968 A1 | 10/2002 | Zilla et al. | |
| 2003/0018294 A1 | 1/2003 | Cox | |
| 2003/0060782 A1 | 3/2003 | Bose et al. | |
| 2003/0093111 A1 | 5/2003 | Ken et al. | |
| 2003/0171801 A1 | 9/2003 | Bates | |
| 2003/0229286 A1 | 12/2003 | Lenker | |
| 2003/0229393 A1 | 12/2003 | Kutryk et al. | |
| 2003/0233141 A1 | 12/2003 | Israel | |
| 2004/0029268 A1 | 2/2004 | Colb et al. | |
| 2004/0087998 A1 | 5/2004 | Lee et al. | |
| 2004/0116998 A1 | 6/2004 | Erbel et al. | |
| 2004/0138736 A1 * | 7/2004 | Obara | 623/1.16 |
| 2004/0170685 A1 | 9/2004 | Carpenter et al. | |
| 2004/0172121 A1 | 9/2004 | Eidenschink et al. | |
| 2004/0186562 A1 | 9/2004 | Cox | |
| 2004/0193206 A1 | 9/2004 | Gerberding et al. | |
| 2004/0204754 A1 * | 10/2004 | Kaplan et al. | 623/1.16 |
| 2005/0010281 A1 * | 1/2005 | Yodfat et al. | 623/1.39 |
| 2005/0043787 A1 | 2/2005 | Kutryk et al. | |
| 2005/0075716 A1 | 4/2005 | Yan | |
| 2005/0096725 A1 | 5/2005 | Pomeranz et al. | |
| 2005/0124896 A1 | 6/2005 | Richter et al. | |
| 2005/0137677 A1 | 6/2005 | Rush | |
| 2005/0137680 A1 | 6/2005 | Ortiz et al. | |
| 2005/0154447 A1 * | 7/2005 | Goshgarian | 623/1.15 |
| 2005/0154448 A1 | 7/2005 | Cully et al. | |
| 2005/0171593 A1 | 8/2005 | Whirley et al. | |
| 2005/0267568 A1 | 12/2005 | Berez et al. | |
| 2005/0283220 A1 | 12/2005 | Gobran et al. | |
| 2006/0020322 A1 | 1/2006 | Leynov et al. | |
| 2006/0036311 A1 | 2/2006 | Nakayama et al. | |
| 2006/0106421 A1 | 5/2006 | Teoh | |
| 2006/0121080 A1 | 6/2006 | Lye et al. | |
| 2006/0136037 A1 | 6/2006 | DeBeer et al. | |
| 2006/0142849 A1 | 6/2006 | Killion et al. | |

(56) References Cited

U.S. PATENT DOCUMENTS

| | | |
|---|---|---|
| 2006/0149355 A1 | 7/2006 | Mitelberg et al. |
| 2006/0155355 A1 | 7/2006 | Jung |
| 2006/0173530 A1 | 8/2006 | Das |
| 2006/0200230 A1 | 9/2006 | Richter |
| 2006/0200234 A1 | 9/2006 | Hines |
| 2006/0206199 A1 | 9/2006 | Churchwell et al. |
| 2006/0217799 A1 | 9/2006 | Mailander et al. |
| 2006/0224237 A1 | 10/2006 | Furst et al. |
| 2006/0259123 A1 | 11/2006 | Dorn |
| 2006/0265051 A1 | 11/2006 | Caro et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0287710 A1 | 12/2006 | Lendlein et al. |
| 2007/0038288 A1 | 2/2007 | Lye et al. |
| 2007/0083258 A1 | 4/2007 | Falotico et al. |
| 2007/0088387 A1 | 4/2007 | Eskridge et al. |
| 2007/0088425 A1* | 4/2007 | Schaeffer ............... 623/1.13 |
| 2007/0112415 A1 | 5/2007 | Bartlett |
| 2007/0150045 A1* | 6/2007 | Ferrera ............... 623/1.11 |
| 2007/0173921 A1* | 7/2007 | Wholey et al. ............... 623/1.13 |
| 2007/0213800 A1 | 9/2007 | Fierens et al. |
| 2007/0276477 A1 | 11/2007 | Lee et al. |
| 2007/0288083 A1 | 12/2007 | Hines |
| 2008/0004653 A1 | 1/2008 | Sherman et al. |
| 2009/0054966 A1 | 2/2009 | Rudakov et al. |

FOREIGN PATENT DOCUMENTS

| | | |
|---|---|---|
| EP | 0947204 | 10/1999 |
| EP | 1121911 | 8/2001 |
| EP | 1 129 666 | 9/2001 |
| EP | 1391184 | 2/2004 |
| EP | 1 470 795 | 10/2004 |
| EP | 1543798 | 6/2005 |
| EP | 1 550 477 | 7/2005 |
| EP | 1797844 | 6/2007 |
| JP | 1254623 | 10/1989 |
| WO | WO 98/14137 | 4/1998 |
| WO | WO 9902092 | 1/1999 |
| WO | WO 9958084 | 11/1999 |
| WO | WO 9962432 | 12/1999 |
| WO | WO 0001308 | 1/2000 |
| WO | WO 00-06145 | 2/2000 |
| WO | WO 0047134 | 8/2000 |
| WO | WO 0051522 | 9/2000 |
| WO | WO 0056247 | 9/2000 |
| WO | WO 0166167 | 9/2001 |
| WO | WO 0187184 | 11/2001 |
| WO | WO 0193782 | 12/2001 |
| WO | WO 0103607 | 1/2002 |
| WO | WO 02-022024 | 3/2002 |
| WO | WO 02-051336 | 7/2002 |
| WO | WO 02/069783 | 9/2002 |
| WO | WO 02/078764 | 10/2002 |
| WO | WO 03049600 | 6/2003 |
| WO | WO 03/065881 | 8/2003 |
| WO | WO 2004000379 | 12/2003 |
| WO | WO 2004-028405 | 4/2004 |
| WO | WO 2005/000165 | 1/2005 |
| WO | WO 2005-065580 | 7/2005 |
| WO | WO 2005-086831 | 9/2005 |
| WO | WO 2005094725 | 10/2005 |
| WO | WO 2005094726 | 10/2005 |
| WO | WO 2006033641 | 3/2006 |

OTHER PUBLICATIONS

Reul, J. et al., Long-Term Angiographic and Histopathologic Findings in Experimental Aneurysms of the Carotid Bifurcation Embolized with Platinum and Tungsten Coils, American Journal of Neuroradiology, Jan. 1997, 35-42, vol. 18.

* cited by examiner

METHOD FOR TREATING ANEURYSMS

RELATED APPLICATIONS

This application is a U.S. National Phase of International Application No. PCT/SG2004/000338, filed Oct. 15, 2004, designating the U.S. and published in English on Oct. 13, 2005 as WO 2005/094725, which claims the benefit of Singapore Application No. 200401735-6, filed Mar. 31, 2004.

TECHNICAL FIELD

The invention concerns a method for treating bifurcation or trifurcation aneurysms. In particular, the method is suitable for bifurcation or trifurcation aneurysms with wide aneurysm necks.

BACKGROUND OF THE INVENTION

An aneurysm is a bulge or a weakening of a wall of an artery. An aneurysm usually occurs where one main blood vessel splits into two (bifurcation) or three smaller vessels (trifurcation). Bifurcation aneurysms account for approximately 35% of all cases of intracranial hemorrhagic disease.

Aneurysms may burst and cause bleeding into a covering around the brain called the subarachnoid space. This is referred to as a subarachnoid hemorrhage. Subarachnoid hemorrhage secondary to a ruptured aneurysm causes a severe headache.

Therefore, there is a desire for minimally invasive, less traumatic methods to treat bifurcation and trifurcation aneurysms.

SUMMARY OF THE INVENTION

In a first preferred aspect, there is provided a method for treating a bifurcation aneurysm, the aneurysm having an aneurysm neck, the method comprising:
    positioning a first mechanically expandable device in a first bifurcation branch proximate to the aneurysm neck;
    positioning a second mechanically expandable device in a second bifurcation branch proximate to the aneurysm neck; and
    expanding the mechanically expandable devices to constrict the aneurysm neck such that blood circulation to the bifurcation aneurysm is reduced.

The aneurysm neck may be constricted such that blood circulation to the aneurysm is completely interrupted.

The mechanically expandable devices may be stents.

The stents may be mechanically expanded such that blood circulation to the bifurcation aneurysm via the aneurysm neck may be occluded.

The aneurysm may be reduced further in size by deploying gels or using coils. Where the aneurysm neck is wide, coils or securing glues may be deployed inside the aneurysm to reduce blood circulation inside the aneurysm. An aneurysm neck may be wide if the ratio of the diameter of the dome of the aneurysm to the width of the aneurysm neck is less than two.

The stents may be balloon expandable or self-expandable.

The stents may have markers to facilitate precise positioning in the branches. The markers may be placed at the distal and proximal ends of the stents. The markers may be radiopaque. The markers may be made from gold or platinum.

The stents may be positioned in the branches sequentially. The stents may be expanded at the same time. Alternatively, the stents may be expanded sequentially.

The stent may be tapered towards the distal end of the stent. The stent may have a trapezoidal longitudinal cross-section. The stent may have proximal end struts that are elongated relative to the remaining struts.

The first stent may be positioned partially within the first bifurcation branch such that a portion of the proximal end of the first stent is not introduced within the first bifurcation branch.

The second stent may be positioned partially within the second bifurcation branch such that a portion of the proximal end of the second stent is not introduced within the second bifurcation branch.

A balloon of a balloon catheter may be used to expand the stent during deployment. The balloon may be tapered such that the proximal end of the stent is expanded first during deployment. Advantageously, this allows the aneurysm neck to be bridged with greater effectiveness.

The balloon may be made of soft durometer thin nylon or silicon.

The first stent may be expanded by a first balloon and the second stent may be expanded by a second balloon. The first and second balloons may be on a single shaft of a balloon catheter. The stents may be expanded at the same time during deployment.

Additional angioplasty balloon expansion may be used to secure the deployment of the stents.

The stents may be connected by a membrane for obstructing blood circulation to the bifurcation aneurysm. The membrane may comprise at least one layer of an elastomeric polymer. The membrane may comprise receptacles for carrying drugs or reagents for subsequent release after the stents are deployed. The drugs or reagents may include substances that reduce the thrombogenic, inflammatory or smooth muscle cell proliferative response of the vessel to the implantable medical devices. For example, cell inhibitors can be delivered in order to inhibit smooth muscle cells proliferation. In intracranial or some other applications fibrin sealants can be used and delivered to seal aneurysm neck and provide fibroblasts and endothelial cells growth. Specific examples of drugs or reagents may include heparin, phosporylcholine, albumin, dexamethasone, paclitaxel and vascular endothelial growth factor (VEGF).

In a second aspect, there is provided a method for treating a trifurcation aneurysm, the aneurysm having an aneurysm neck, the method comprising:
    positioning a first mechanically expandable device in a first trifurcation branch proximate to the aneurysm neck;
    positioning a second mechanically expandable device in a second trifurcation branch proximate to the aneurysm neck;
    positioning a third mechanically expandable device in a third trifurcation branch proximate to the aneurysm neck; and
    expanding the mechanically expandable devices to constrict the aneurysm neck such that blood circulation to the trifurcation aneurysm is reduced.

The first mechanically expandable device may be positioned partially within the first trifurcation branch such that a portion of the proximal end of the first mechanically expandable device is not introduced within the first trifurcation branch.

The second mechanically expandable device may be positioned partially within the second trifurcation branch such that a portion of the proximal end of the second mechanically expandable device is not introduced within the second trifurcation branch.

The third mechanically expandable device may be positioned partially within the third trifurcation branch such that a portion of the proximal end of the third mechanically expandable device is not introduced within the third trifurcation branch.

In a third aspect, there is provided a system for treating a bifurcation aneurysm, the aneurysm having an aneurysm neck, the system comprising:
  a first mechanically expandable device positioned in a first bifurcation branch proximate to the aneurysm neck;
  a second mechanically expandable device positioned in a second bifurcation branch proximate to the aneurysm neck; and
  wherein the mechanically expandable devices are expanded to constrict the aneurysm neck such that blood circulation to the bifurcation aneurysm is reduced.

In a fourth aspect, there is provided a system for treating a trifurcation aneurysm, the aneurysm having an aneurysm neck, the system comprising:
  a first mechanically expandable device positioned in a first trifurcation branch proximate to the aneurysm neck;
  a second mechanically expandable device positioned in a second trifurcation branch proximate to the aneurysm neck;
  a third mechanically expandable device positioned in a third trifurcation branch proximate to the aneurysm neck; and
  wherein the mechanically expandable devices are expanded to constrict the aneurysm neck such that blood circulation to the trifurcation aneurysm is reduced.

In a fifth aspect, there is provided a mechanically expandable device for treating a bifurcation or trifurcation aneurysm, the aneurysm having an aneurysm neck, the device comprising:
  a generally tubular structure having an exterior surface defined by a plurality of interconnected struts having interstitial spaces therebetween, said generally tubular structure expandable from a first position to a second position, and said tubular structure is expanded radially outwardly to the second position such that the exterior surface of said structure engages with the inner surface of a bifurcation or trifurcation branch so as to maintain a fluid pathway through said branch and to constrict the aneurysm neck such that blood circulation to the aneurysm is reduced;
  wherein a proximal portion of the struts are elongated relative to the remaining struts such that the device is tapered towards its distal end after deployment in the branch.

In a sixth aspect, there is provided a balloon for expanding a mechanically expandable device for treating a bifurcation or trifurcation aneurysm, the balloon being connected to a balloon catheter for inflation, and the device comprising a interconnected struts at its proximal end that are elongated relative to the remaining struts of the device such that the device is tapered towards its distal end after deployment in a bifurcation or trifurcation branch;
  wherein the balloon is tapered towards its distal end after inflation, and the inflation of the balloon causes the elongated struts of the device to expand at a greater rate than the remaining struts for constricting the aneurysm neck such that blood circulation to the aneurysm is reduced.

The balloon may be a first balloon used in combination with a second balloon to expand a second mechanically expandable device in another bifurcation or trifurcation branch. The first balloon and second balloon may be inflated together via a single balloon catheter

BRIEF DESCRIPTION OF THE DRAWINGS

An example of the invention will now be described with reference to the accompanying drawings, in which.

DETAILED DESCRIPTION OF THE DRAWINGS

Figure 1:
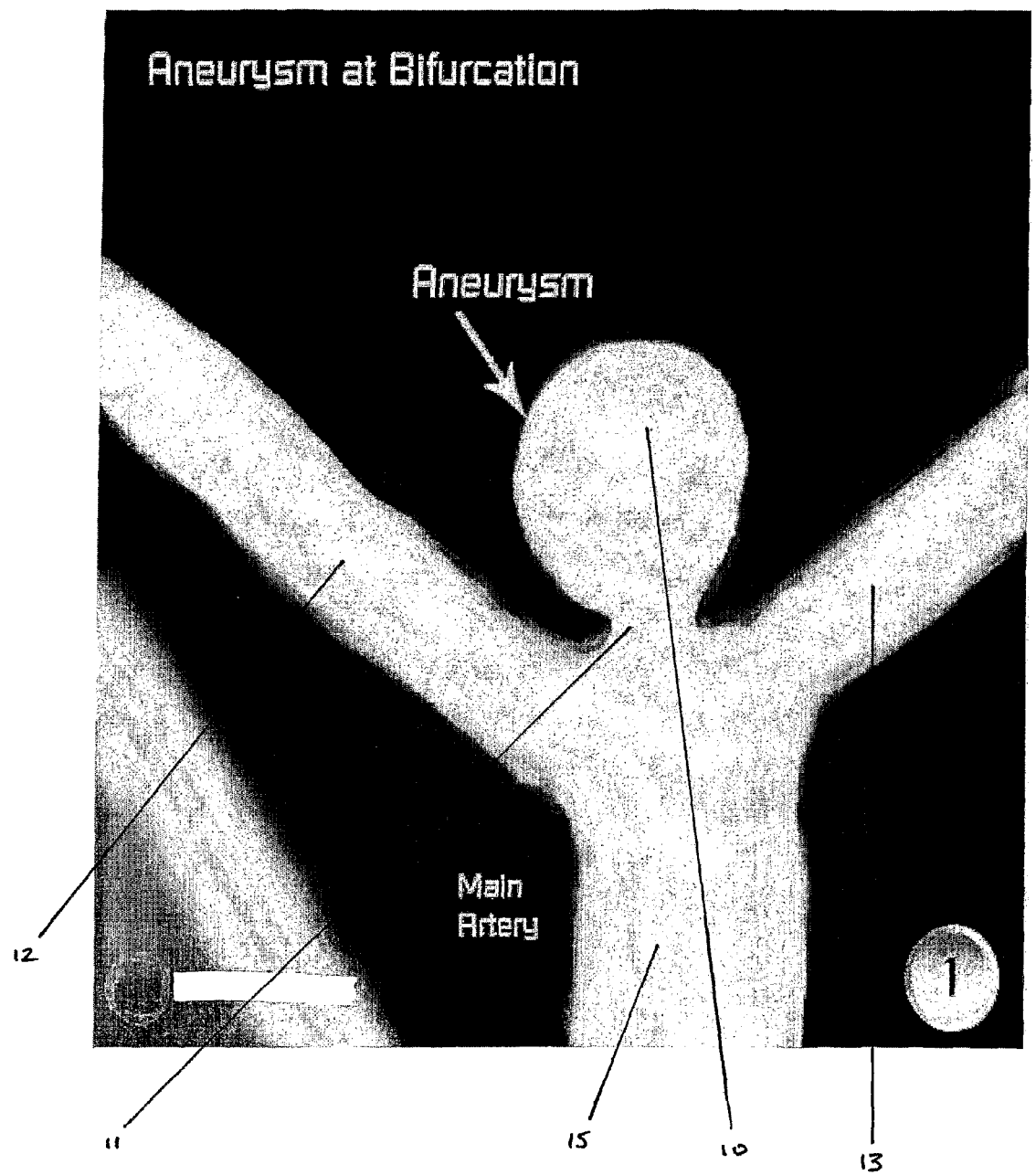
FIG. 1 is a pictorial representation of a bifurcation aneurysm.
Figure 2:
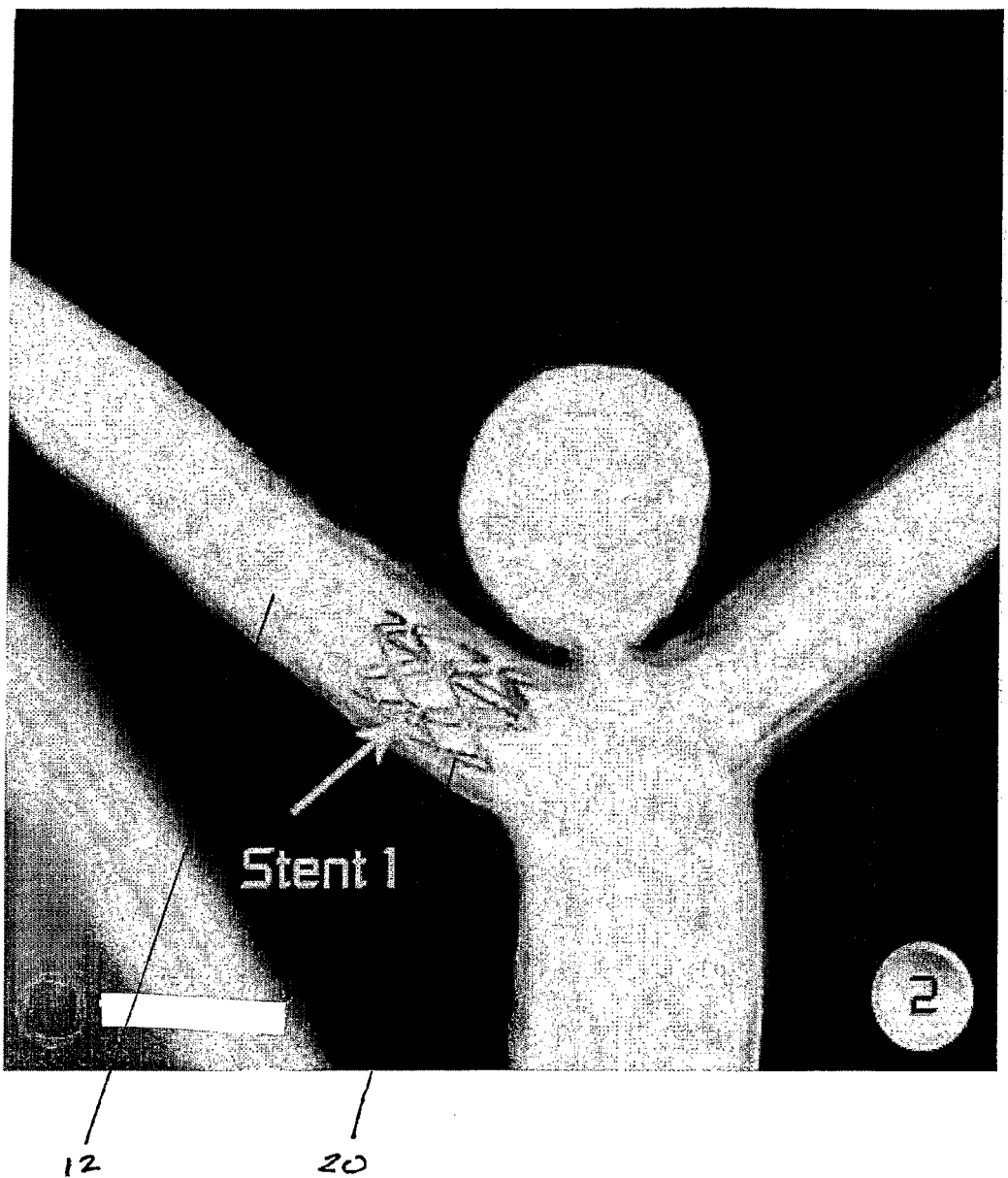
FIG. 2 is a pictorial representation of a stent deployed in a bifurcation branch.
Figure 3:
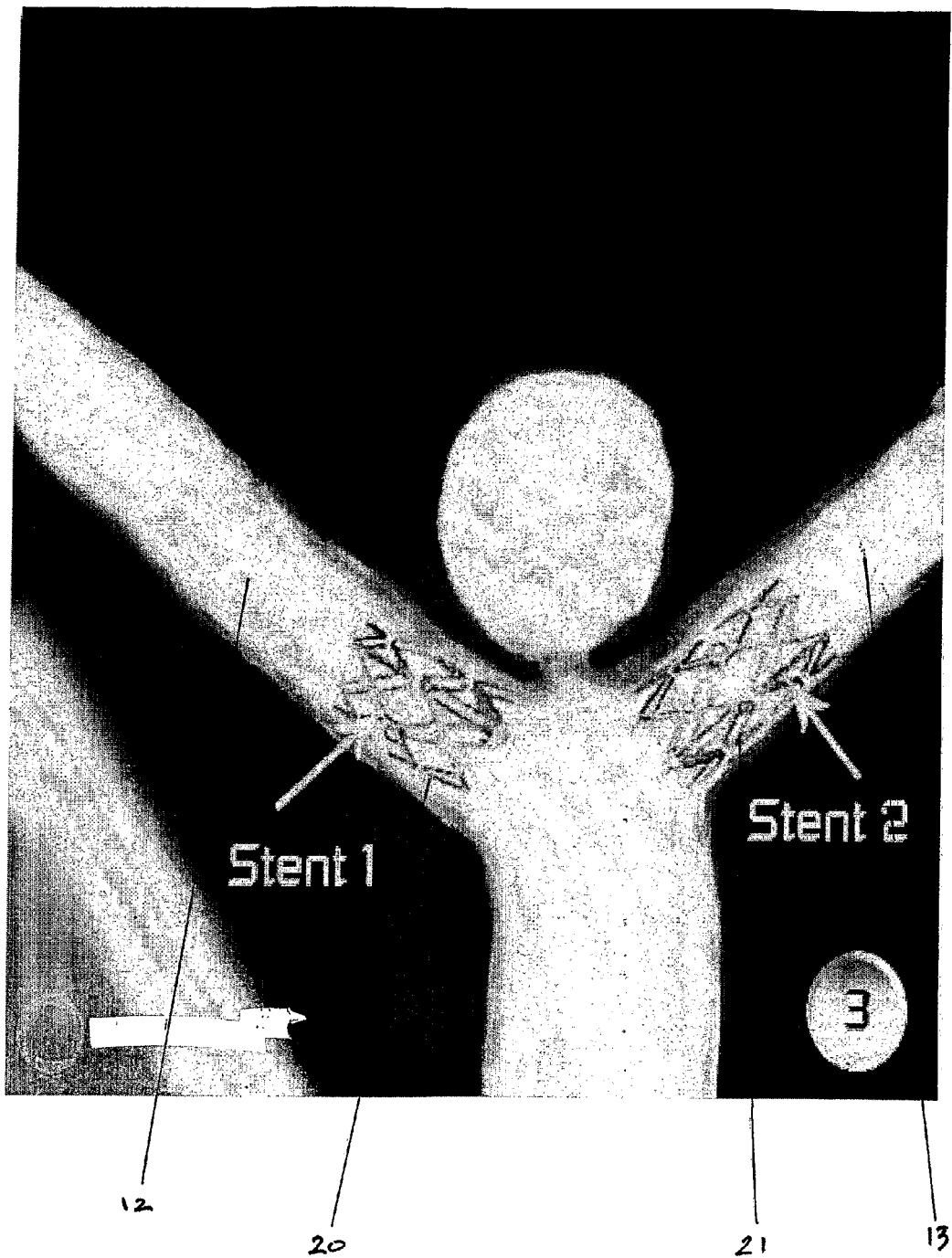
FIG. 3 is a pictorial representation of stents deployed in both bifurcation branches.
Figure 4:
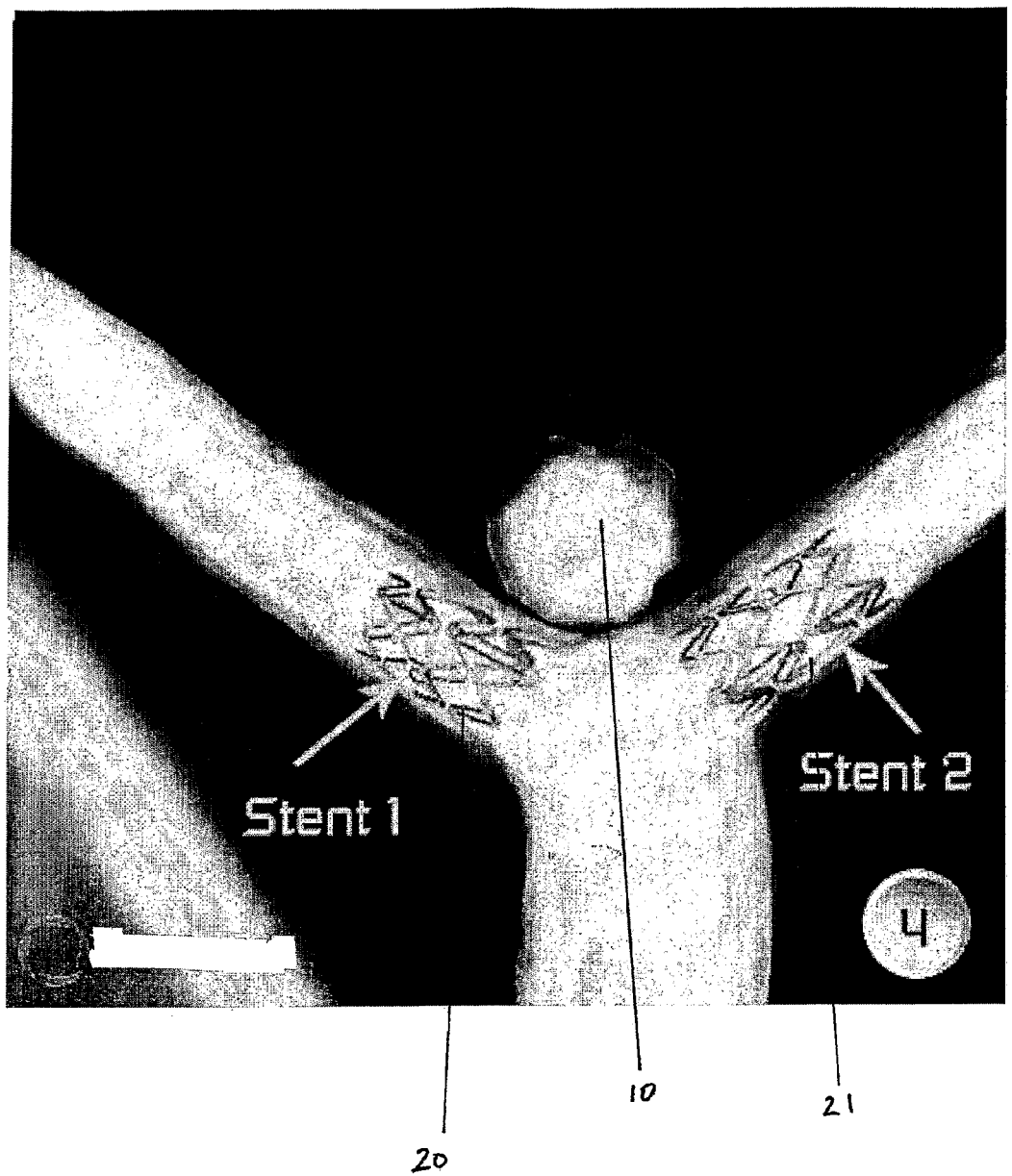
FIG. 4 is a pictorial representation of a reduction of blood circulation to the bifurcation aneurysm when the stents are expanded.
Figure 5:
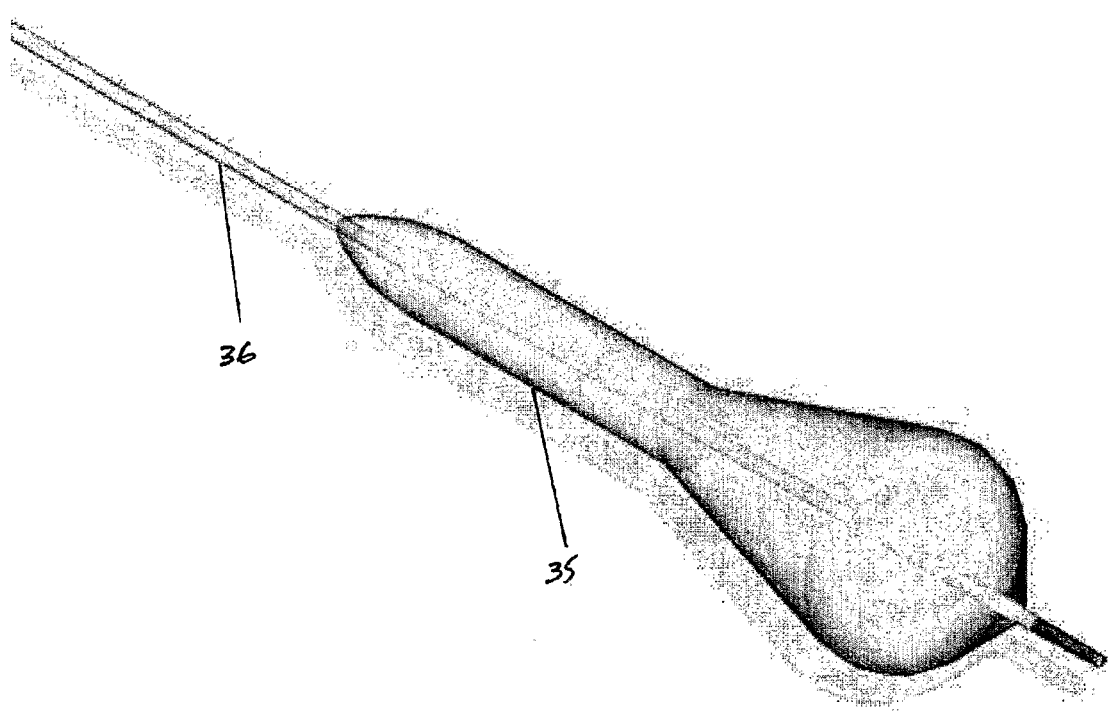
FIG. 5 is a pictorial representation of a tapered balloon to deploy the stent in a bifurcation branch.
Figure 6:
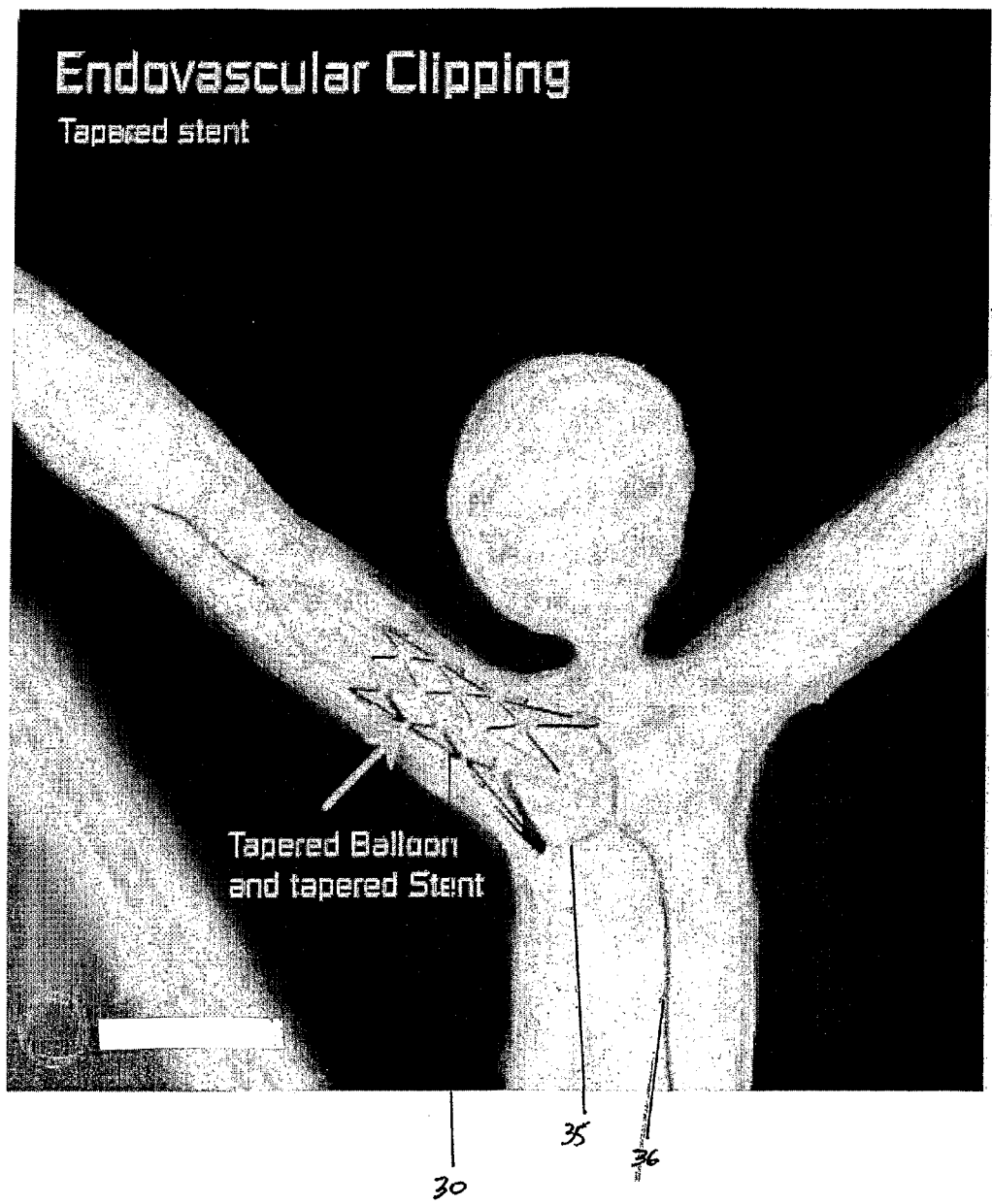
FIG. 6 is a pictorial representation of a tapered stent being deployed by a tapered balloon in a bifurcation branch.
Figure 7:
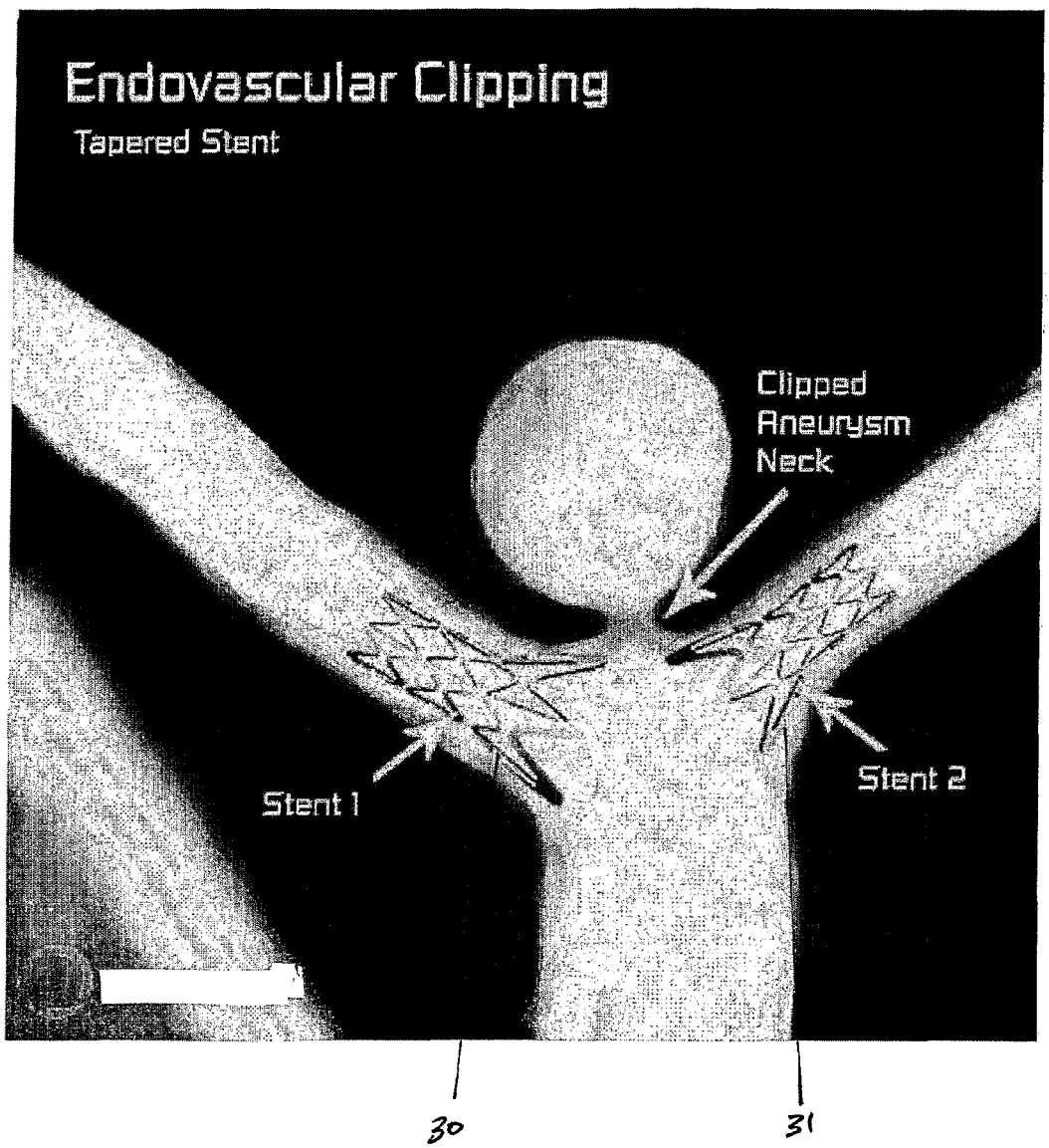
FIG. 7 is a pictorial representation of tapered stents deployed in both bifurcation branches.

Referring to FIG. 1, a method for treating a bifurcation aneurysm 10 is shown. The aneurysm 10 has an aneurysm neck 11 where blood passes from a main artery 15 to the aneurysm 10. The aneurysm 10 is located at the end of the main artery 15 where it diverges into two bifurcation branches 12, 13. A first stent 20 is positioned in a first bifurcation branch 12 proximate to the aneurysm neck 11 as shown in FIG. 2. Next, a second stent 21 is positioned in a second bifurcation branch 13 proximate to the aneurysm neck 11 as shown in FIG. 3. The stents 12, 13 are expanded to constrict the aneurysm neck 11 such that blood circulation to the aneurysm 10 is reduced. In a bifurcation branch 12, 13, the side of the branch wall 12, 13 opposing the aneurysm neck 11 is more rigid relative to the branch wall 12, 13 adjacent to the aneurysm neck 11. Thus, when the stent 20, 30 is expanded, the majority of the expansion force is directed towards the branch wall 12, 13 adjacent to the aneurysm neck 11 which begins to constrict the aneurysm neck 11. Even if the aneurysm neck 11 is partially constricted, blood circulation to the aneurysm 10 is reduced. This eventually leads to the aneurysm 10 drying out from a reduction in blood circulation as shown in FIG. 4.

Intracranial stents 20, 30 are designed to be very flexible, and have a low profile (0.033" to 0.034" or even less as crimped onto delivery catheter) and thin wall (0.0027" to 0.0028"). The intracranial stents 20, 30 feature low deployment pressure (3 to 4 atmospheres) and do not necessarily have the highest possible radial strength because there is no need for high strength in intracranial applications. In one example, the stents 20, 30 are made from platinum/iridium/tungsten alloys.

Stents 20, 30 are a generally tubular structure having an exterior surface defined by a plurality of interconnected struts 32 having interstitial spaces there between. The generally tubular structure is expandable from a first position, wherein the stent 20, 30 is sized for intravascular insertion, to a second position, wherein at least a portion of the exterior surface of the stent contacts the vessel wall 12, 13. The expansion of the stent 20, 30 is accommodated by flexing and bending of the interconnected struts 32 throughout the generally tubular structure. It is contemplated that many different stent designs can be produced. A myriad of strut patterns are known for achieving various design goals such as enhancing strength, maximizing the expansion ratio or coverage area, enhancing longitudinal flexibility or longitudinal stability upon expansion. One pattern may be selected over another in an effort to optimize those parameters that are of particular importance for a particular application.

In one example, the stent 20, 30 comprises stent struts 32 of a ring, ring connectors, and end markers 34. The stents 100 are made of multiple circumstantial rings, where the ring connectors connect two or three adjacent rings to hold the rings in place. In another example, a self-expanding stent 20, 30 is made of wires/ribbons. While a self-expanding stent may have many designs, one specific stent 20, 30 has a typical braided pattern with welded ends. The stent 20, 30 is designed such that it is relatively flexible along its longitudinal axis to facilitate delivery through tortuous body lumens, but is sufficiently stiff and stable radially in an expanded condition to maintain the patency of a body lumen, such as an artery or bifurcation/trifurcation branch 12, 13 when implanted therein. When a tubular stent 20, 30 is fully expanded to its deployed diameter, the latticework of struts 32 takes on a shape in which adjacent crests undergo wide separation, and portions of the struts 32 take on a transverse, almost fully lateral orientation relative to the longitudinal axis of the stent 20, 30. Such lateral orientation of a plurality of the struts 32 enables each fully opened cell to contribute to the firm mechanical support offered by the stent 20, 30 in its fully deployed position, to assure a rigid structure which is highly resistant to recoil of the vessel wall 12, 13 following stent deployment. It bears emphasis, however, that the configuration of this stent structure, while highly desirable, is illustrative only.

Figure 8:
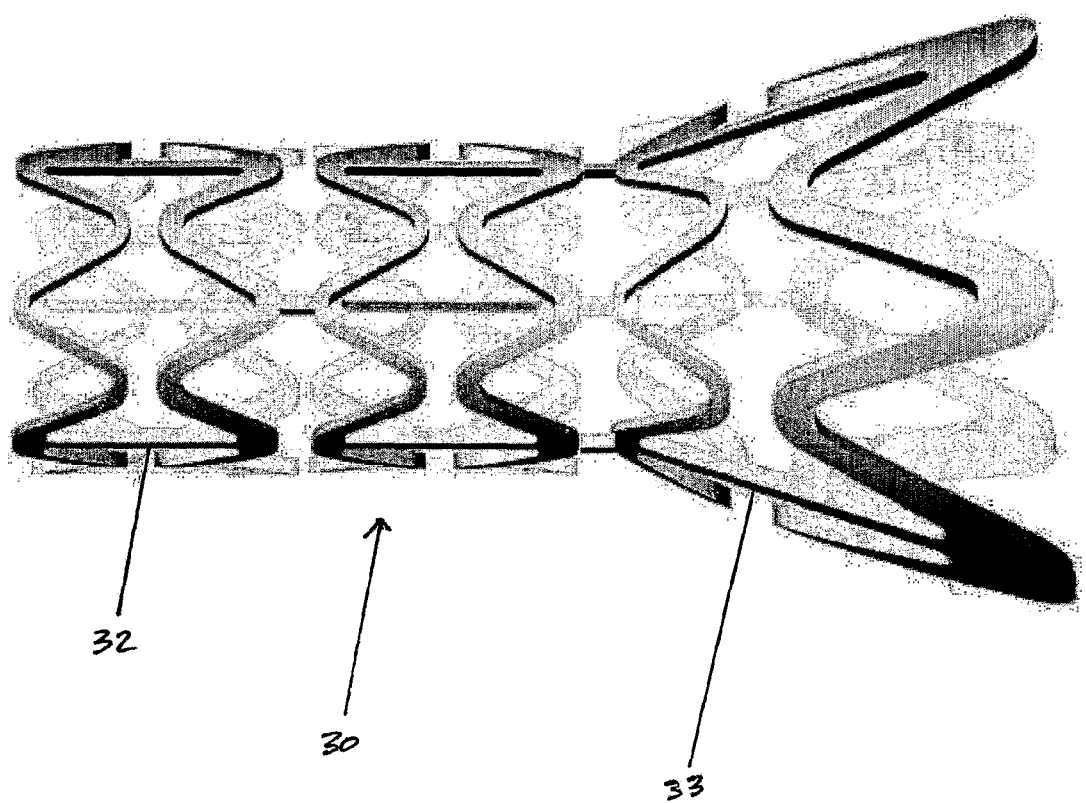
FIG. 8 is a pictorial representation of a tapered stent with elongated end struts when deployed.
Figure 9:
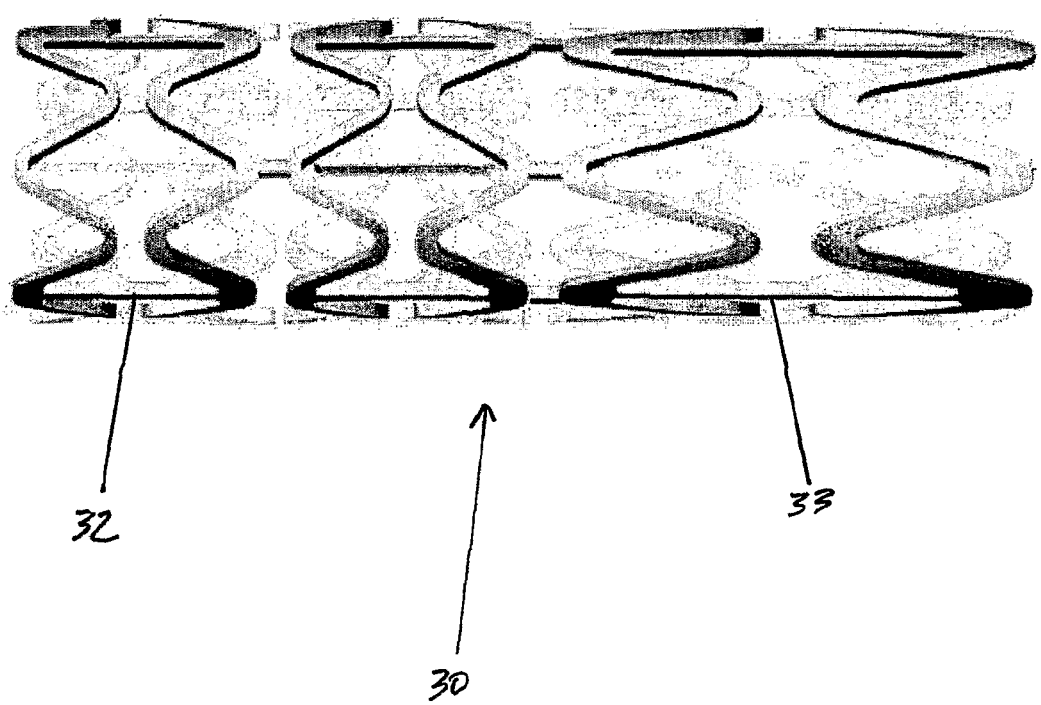
FIG. 9 is a pictorial representation of a tapered stent with elongated end struts before deployment.

Referring to FIGS. 5 to 9, tapered stents 30, 31 are used to further enhance constriction of the aneurysm neck 11. For the delivery system, a tapered balloon 35 of a balloon catheter 36 expands the tapered stents 30, 31 by inflation, after the stents 30, 31 are placed into position in a respective bifurcation branch 12, 13. At the proximal end of the tapered stents 30, 31 there are elongated struts 33 to provide the tapering effect. The elongated struts 33 expand at a greater rate relative to the non-elongated struts 32. Also, tapered stents 30, 31 after deployment have a profile which conforms to the opening of the bifurcation branch 12, 13 from the main artery 15. FIG. 8 depicts a tapered stent 30 in an expanded state, typically when the stent 30 is deployed. FIG. 9 depicts the tapered stent 30 in a compressed state, typically during delivery via the balloon catheter 36.

The delivery system includes a guide wire lumen, a balloon inflating lumen, a connector, a balloon catheter shaft, and platinum marker bands on the catheter shaft (not shown). The guide wire lumen is used for introducing a guide wire in a balloon catheter 36, and the balloon inflating lumen is used for inflating the balloon 35 after the stent 20, 30 to be placed reaches its targeted location. The connector is used for separating the guide wire lumen and the balloon inflating lumen. The balloon catheter shaft carries the guide wire lumen and the balloon inflating lumen separately, with a typical length ranging 135 to 170 cm. The ring markers on the catheter shaft are used for showing the start of balloon tapers 35 and the edges of the stent 20, 30.

The balloon 35 is formed of suitable materials such as irradiated polyethylene, polyethylene terephthalate, polyvinylchloride, nylon, and copolymer nylons such as Pebax™. Other polymers may also be used. In order for the stent 20, 30 to remain in place on the balloon 35 during delivery to the desired site within a branch 12, 13, the stent 20, 30 is crimped onto the balloon 35.

In a preferred embodiment, the delivery of the stent 20, 30 is accomplished in the following manner. The stent 20, 30 is first mounted onto the inflatable balloon 35 on the distal extremity of the delivery catheter 36. The stent 20, 30 is mechanically crimped onto the exterior of the folded balloon 35. The catheter/stent assembly is introduced within vasculature through a guiding catheter. A guide wire is disposed across the diseased arterial section and then the catheter/stent assembly is advanced over a guide wire within the branch 12, 13 until the stent 20, 30 reaches the desired position. The balloon 35 of the catheter 36 is expanded, expanding the stent 20, 30 against the branch wall 12, 13. The expanded stent serves to hold open the artery after the catheter is withdrawn. Due to the formation of the stent 20, 30 from an elongated tube, the undulating component of the cylindrical elements of the stent 20, 30 is relatively flat in transverse cross-section, so that when the stent 20, 30 is expanded, the cylindrical elements are pressed against the wall of the branch 12, 13 and as a result do not interfere with the blood flow through the branch 12, 13. The cylindrical elements of the stent 20, 30 which are pressed into the wall of the branch 12, 13 is eventually covered with an endothelial cell layer which further minimizes blood flow interference. Furthermore, the closely spaced cylindrical elements at regular intervals provide uniform support for the wall of the branch 12, 13, and consequently are well adopted to take up and hold in place small flaps or dissections in the wall of the branch 12, 13.

As described earlier, a stent 20, 30 may be deployed by radial expansion under outwardly directed radial pressure exerted. For example by active inflation of a balloon 35 of a balloon catheter 36 on which the stent 20, 30 is mounted. Another deployment method may rely on the stent 20, 30 being self-expandable. In some instances, passive spring characteristics of a preformed elastic (that is, self-opening) stent 20, 30 serve the purpose. The stent 20, 30 is then expanded to engage the inner lining or inwardly facing surface of the vessel wall 12, 13 with sufficient resilience to allow some contraction but also with sufficient stiffness to largely resist the natural recoil of the vessel wall 12, 13.

For resilient or self-expanding stents 20, 30, they are deployed without dilation balloons 35. Self-expanding stents 20, 30 are pre-selected according to the diameter of the blood vessel, bifurcation/trifurcation branch 12, 13 or other intended fixation site. While stent deployment requires skill in stent positioning, such deployment does not require the additional skill of carefully dilating a balloon 35 to plastically expand the prosthesis to the appropriate diameter. Further, the self-expanding stent 20, 30 remains at least slightly elastically compressed after fixation, and has a restoring force which facilitates acute fixation. By contrast, a plastically expanded stent 20, 30 must rely on the restoring force of deformed tissue, or on hooks, barbs, or other independent fixation elements.

Figure 15:
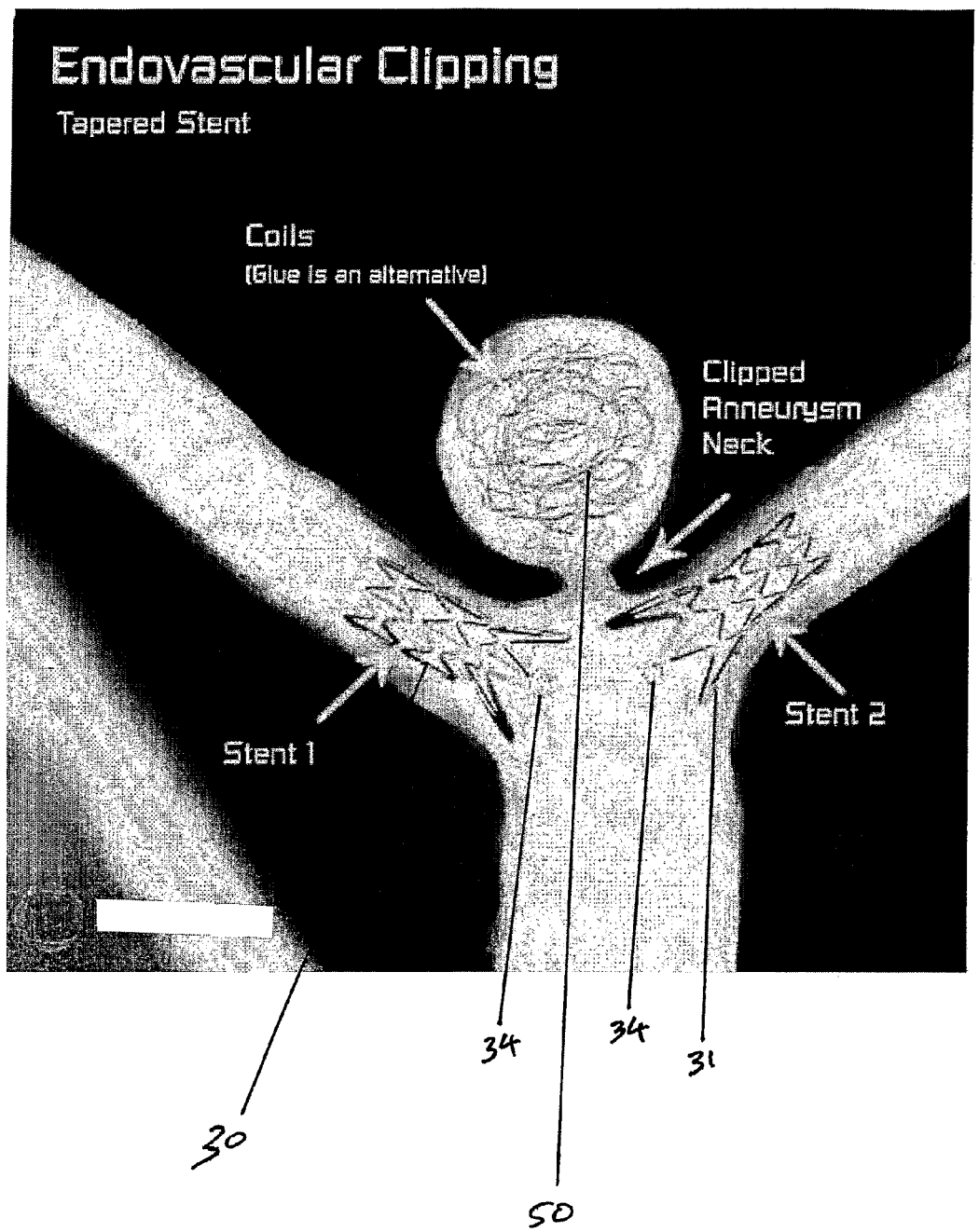
FIG. 15 is a pictorial representation of coils deployed in the aneurysm in addition to tapered stents with markers deployed in both bifurcation branches.

Referring to FIG. 15, in a further example, the aneurysm 10 is reduced further in size by deploying gels or using coils 50. If the aneurysm neck 11 is wide, coils 50 or securing glues (not shown) are deployed inside the aneurysm 10 to reduce blood circulation inside the aneurysm 10. An aneurysm neck 11 can be considered wide if the ratio of the diameter of the dome of the aneurysm 10 to the width of the aneurysm neck 11 is less than two.

Figure 10:
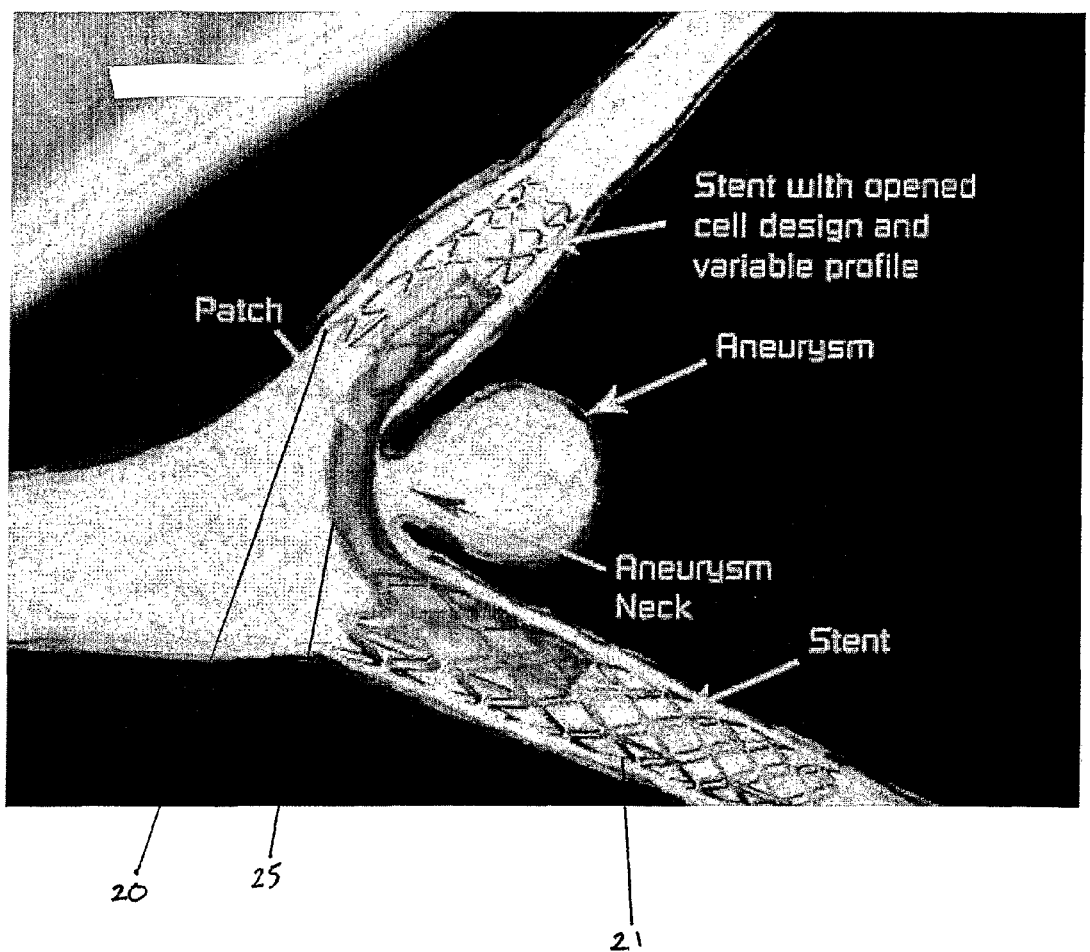
FIG. 10 is a pictorial representation of stents connected by a patch deployed in both bifurcation branches.

Referring to FIG. 10, a pair of stents 20, 21 are joined together by a membrane 25. The membrane 25 obstructs blood circulation to the aneurysm 10. The stents 20, 21 are an open cell design and have a variable profile. Thus in addition to constriction of the aneurysm neck 11 by the stents 20, 21, the presence of the membrane 25 also obstructs blood circulation through the aneurysm neck 11 and may hasten the drying out of the aneurysm 10.

In one example, the membrane 25 may comprise one or more layers of an elastomeric polymer. The membrane 25 may comprise a first layer and a second layer. Many polymeric materials are suitable for making the layers of the membrane 25. One such material may be elastomeric polyurethane. Typically, one first layer is disposed onto the outer surface of a stent 20, 30.

In certain embodiments, the first layer is an independent membrane to mechanically cover and seal the aneurysm 10. In certain embodiments, the first and/or second layers may be made from biodegradable material as a drug or reagent carrier for sustained release.

The intermediate layer may be formed of a material which fuses to the first and second layers or attached to the first layer in a different manner. In certain embodiments, the intermediate layer may be merged with the first layer to form a single layer with recessions within the outer surface of the merged layer.

In one embodiment, the second and intermediate layers are made of biodegradable material that contains drugs or reagents for immediate or sustained controlled release. After biodegradable material has degraded over time, the membrane 25 is still in tact to provide vessel support. The second layer may be made from a polymeric material.

The polymeric layers of the membrane 25 may also be made from a material selected from the group consisting of fluoropolymers, polyimides, silicones, polyurethanes, polyurethanes ethers, polyurethane esters, polyurethaneureas and mixtures and copolymers thereof. Biodegradable polymeric materials can also be used.

Adhering, laminating, suturing or otherwise bonding fusible polymeric layers may be conducted. The fusion of the polymeric layers may be achieved by various techniques such as heat-sealing, solvent bonding, adhesive bonding or use of coatings.

The membrane 25 may further comprise pockets (not shown) serving as receptacles for drugs or reagents so that the drugs or reagents may be delivered into vascular systems. The membrane 25 may cover a part of a stent 20, 30, where the size of the membrane 25 may be varied in accordance with any specific application. In one extreme, the membrane 25 may cover the whole outer surface of a stent 20, 30. Thus, the membrane 25 may be in any shape or size. A drug or reagent can be injected in the form of a gel, liquid or powder into receptacles of the pockets. Alternatively the drug or reagent can be supplied in a powder which has been formed into a solid tablet positioned in the receptacles. Such tablets would gradually dissolve after implantation. The drugs or reagents include substances that reduce the thrombogenic, inflammatory or smooth muscle cell proliferative response of the vessel to the implantable medical devices. For example, cell inhibitors can be delivered in order to inhibit smooth muscle cells proliferation. In intracranial or some other applications fibrin sealants can be used and delivered to seal aneurysm neck and provide fibroblasts and endothelial cells growth. Specific examples of drugs or reagents may include heparin, phosporylcholine, albumin, dexamethasone, paclitaxel and vascular endothelial growth factor (VEGF).

Figure 11:
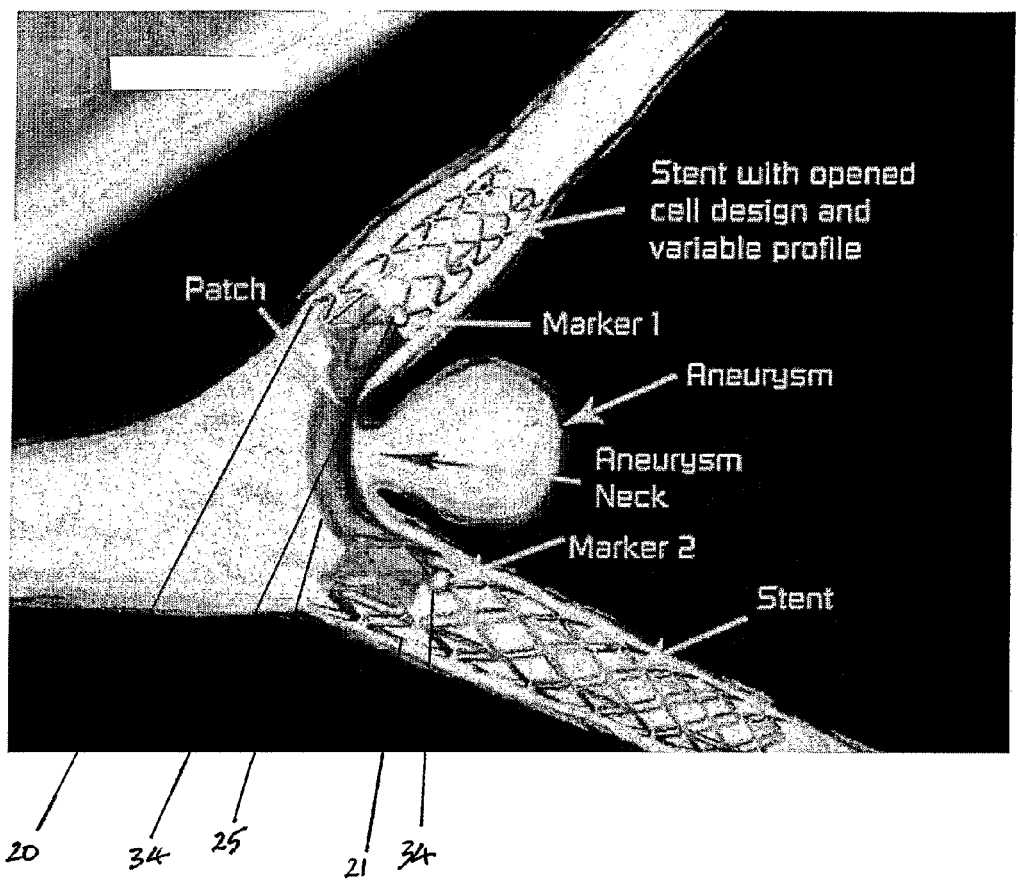
FIG. 11 is a pictorial representation of stents with markers connected by a membrane deployed in both bifurcation branches.
Figure 12:
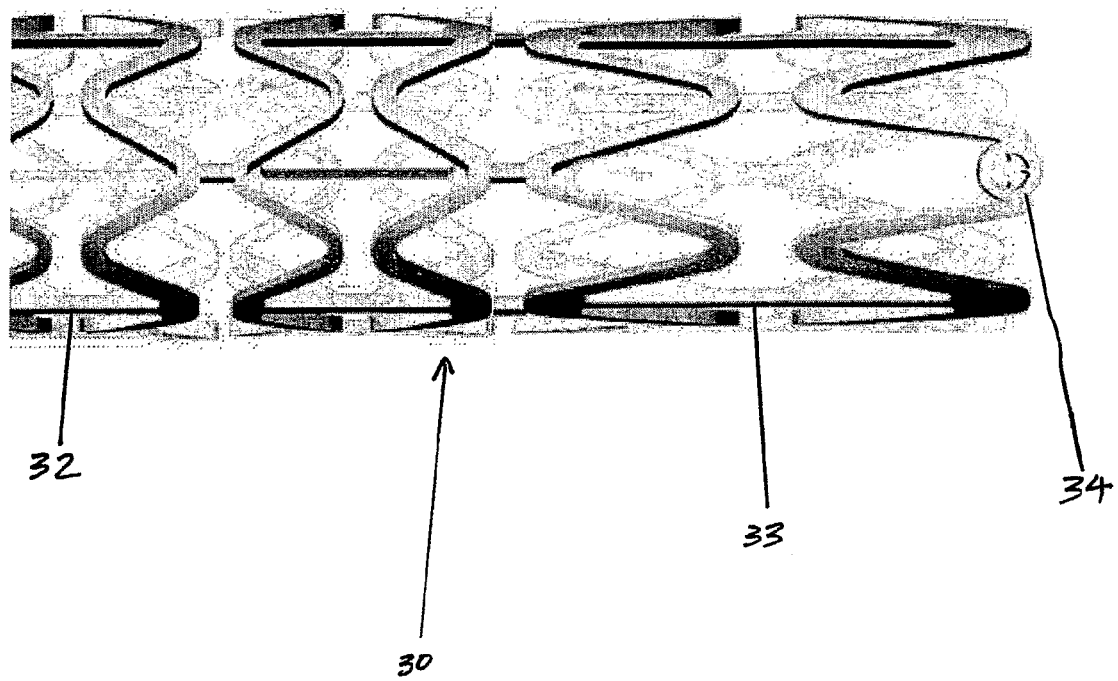
FIG. 12 is a pictorial representation of a tapered stent with elongated end struts and a marker before deployment.

FIGS. 11 and 12 show stents 20, 21, 30, 31 with markers 34. The markers 34 improve visibility as they are radiopaque and may be made from gold or platinum. The markers 34 facilitate precise positioning and orientation of the stents 20, 30 during deployment in the branches 12, 13. The markers 34 may be end markers and are usually placed at the distal and proximal ends of the stents 20, 30. The drawings show a disc shaped marker. However, the shape is not critical so long as the marker 34 can be used to improve visibility of the stent 20, 30. The markers may be center markers that are special type platinum star-shaped markers to assist in precise indication and alignment of the stents 20, 30 in relation to the aneurysm neck 11 and allow further operations with the aneurysm 10. Then, the markers located around the middle of the stent 20, 30. The center markers assist in locating an aneurysm opening during an implantation operation. The center markers can be made of the same material and have the same shape as the end markers.

Figure 13:
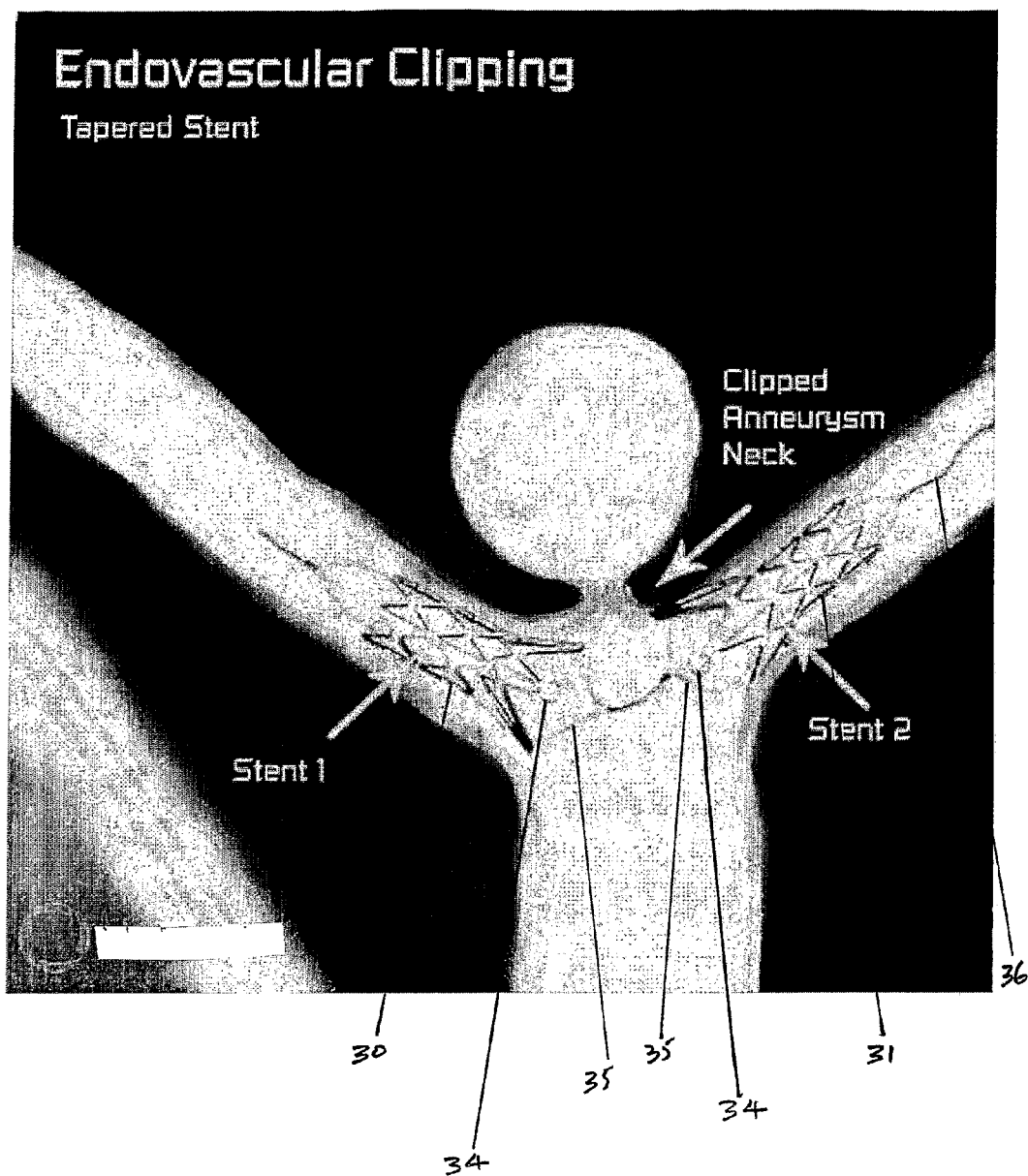
FIG. 13 is a pictorial representation of tapered stents with markers in both bifurcation branches being expanded by two connected tapered balloons.
Figure 14:
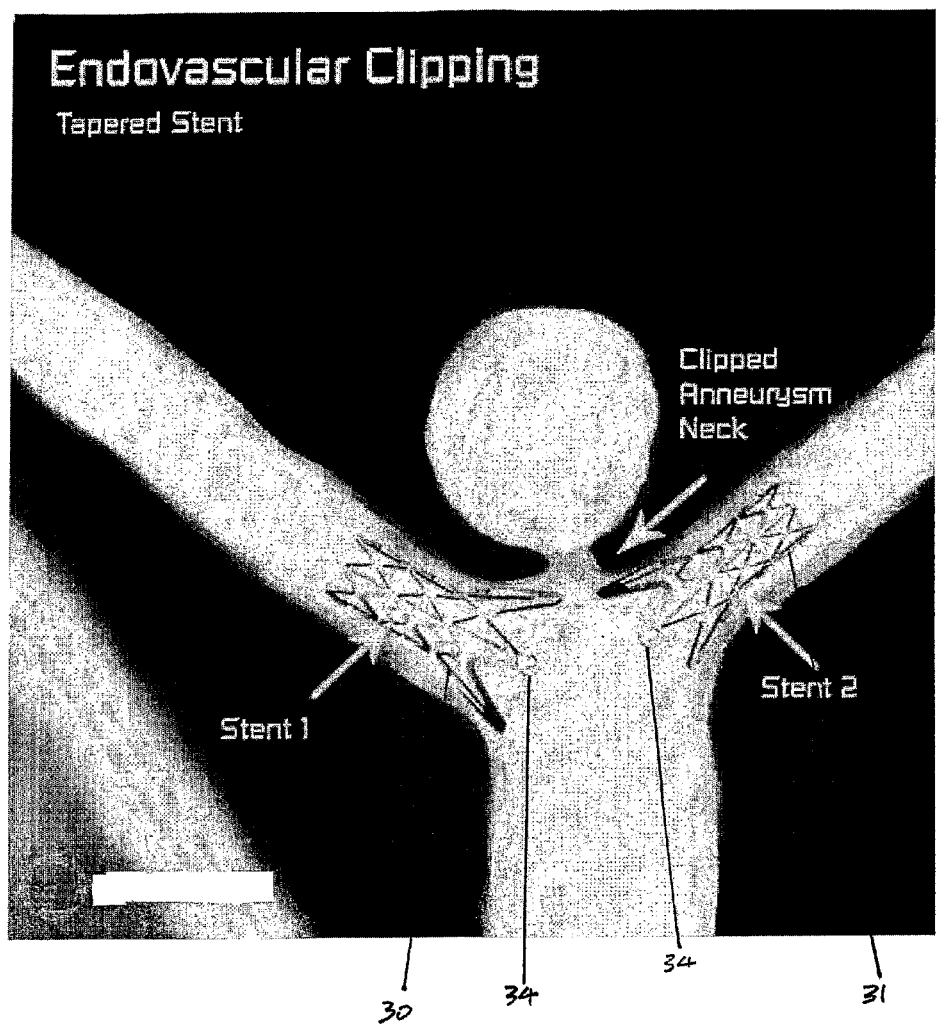
FIG. 14 is a pictorial representation of tapered stents with markers deployed in both bifurcation branches.

FIG. 13 shows tapered stents 30, 31 with markers 34 during deployment. The tapered stents 30, 31 are expanded by two balloons 35 via a single balloon catheter 36. After the tapered stents 30, 31 have been expanded the balloons 35 are deflated and the catheter 36 is retracted as shown in FIG. 14.

Although a bifurcation aneurysm 10 has been described, it is envisaged that the present invention may be used for trifurcation aneurysms and the like.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

I claim:

1. A mechanically expandable device for treating a bifurcation or trifurcation aneurysm, the aneurysm having an aneurysm neck, the device comprising:
 a generally tubular structure having a proximal end, a distal end, and an exterior surface defined by a plurality of interconnected struts forming a series of peaks and valleys having interstitial spaces therebetween, said generally tubular structure expandable from a first position to a second position, and said tubular structure is configured to expand radially outwardly to the second position such that the exterior surface of said structure engages with the inner surface of a bifurcation or trifurcation branch so as to maintain a fluid pathway through said branch and to constrict the aneurysm neck such that blood circulation to the aneurysm is reduced;
 wherein, in the second position, the tubular structure has a cylindrical portion and a tapered portion, the cylindrical portion having a substantially uniform diameter along its longitudinal length, the tapered portion flaring outwardly from the cylindrical portion to the proximal end of the tubular structure, the cylindrical portion comprising a plurality of rings interconnected by a plurality of interconnecting struts, the tapered portion comprising a distalmost ring, a proximalmost ring, and a distal interconnecting strut extending between a peak of the distalmost ring and a valley of the proximalmost ring, the proximalmost ring having a longer longitudinal length than any of the rings in the cylindrical portion, the distal interconnecting strut having a longer longitudinal length than any of the interconnecting struts in the cylindrical portion, and each of the plurality of rings in the cylindrical portion, the distalmost ring, and the proximalmost ring encircling a longitudinal axis of the tubular structure.

2. The device according to claim 1, wherein the tubular structure comprises a self-expanding structure.

3. The device according to claim 1, wherein the tubular structure comprises a plastically deformable structure.

4. The device according to claim 1, wherein the struts comprise at least one material selected from the group consisting of: platinum, iridium, and tungsten.

5. The device according to claim 1, wherein the struts are constructed and arranged in a pattern to achieve, when expanded, one or more of enhanced strength, increased expansion ratio, increased coverage area, enhanced longitudinal flexibility, and enhanced longitudinal stability.

6. The device according to claim 1, wherein the device has a longitudinal axis and wherein at least two of the struts comprise a portion configured to transition to a lateral or near lateral orientation relative to the longitudinal axis when the device is expanded.

7. The device according to claim 1, further comprising at least one marker.

8. The device according to claim 7, wherein the at least one marker comprises a radiopaque marker.

9. The device according to claim 7, wherein the at least one marker is positioned at an end portion of the device or a middle portion of the device.

10. The device according to claim 7, wherein the at least one marker has a disk shape or a star shape.

11. The device according to claim 1, further comprising a coupling strut extending between a valley of the proximalmost ring and a peak of a ring of the cylindrical portion.

12. The device according to claim 11, wherein the coupling strut and the distal interconnecting strut extend along a common, substantially linear path along the exterior surface of the tubular structure.

13. The device according to claim 11, further comprising a proximal interconnecting strut extending between the peak of the cylindrical portion ring and a valley of a second ring of the cylindrical portion, the second ring being proximal to the cylindrical portion ring.

14. The device according to claim 13, wherein the distal interconnecting strut, the proximal interconnecting strut, and the coupling strut extend along a common, substantially linear path along the exterior surface of the tubular structure.

15. The device according to claim 11, wherein the coupling strut and the distal interconnecting strut extend along different, substantially linear paths along the exterior surface of the tubular structure.

16. The device according to claim 1, wherein the distal interconnecting strut longitudinal length is greater than a longitudinal length of the distalmost ring and the longitudinal length of the proximalmost ring.

17. The device according to claim 1, wherein the distalmost ring has a longer longitudinal length than any of the rings in the cylindrical portion.

18. The device according to claim 1, further comprising a second distal interconnecting strut extending between a second peak of the distalmost ring and a second valley of the proximalmost ring, the second distal interconnecting strut being circumferentially spaced apart from the distal interconnecting strut.

19. The device according to claim 18, further comprising first and second coupling struts extending between respective first and second valleys of the proximalmost ring and respective first and second peaks of the cylindrical portion ring.

20. The device according to claim 19, wherein the distal interconnecting strut and the first coupling strut extend along a first common, substantially linear path along the exterior surface of the tubular structure, and wherein the second distal interconnecting strut and the second coupling strut extend along a second common, substantially linear path along the exterior surface of the tubular structure.

* * * * *